(12) United States Patent
Young et al.

(10) Patent No.: US 7,962,223 B2
(45) Date of Patent: Jun. 14, 2011

(54) ABLATION PROBE FOR DRUG RELEASE IN TISSUE ABLATION PROCEDURES

(75) Inventors: Kimbolt Young, Newtonville, MA (US); Steven Walak, Natick, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/271,714

(22) Filed: Nov. 14, 2008

(65) Prior Publication Data

US 2009/0131855 A1 May 21, 2009

Related U.S. Application Data

(60) Provisional application No. 60/988,709, filed on Nov. 16, 2007.

(51) Int. Cl.
*A61N 1/06* (2006.01)

(52) U.S. Cl. .................................... 607/101; 607/120

(58) Field of Classification Search .............. 607/99, 607/101, 120
See application file for complete search history.

(56) References Cited

U.S. PATENT DOCUMENTS

| | | | |
|---|---|---|---|
| 5,419,767 A * | 5/1995 | Eggers et al. | 604/114 |
| 5,447,533 A | 9/1995 | Vachon et al. | |
| 5,472,441 A * | 12/1995 | Edwards et al. | 606/41 |
| 5,980,548 A | 11/1999 | Evans et al. | |
| 6,045,565 A | 4/2000 | Ellis et al. | |
| 6,159,143 A | 12/2000 | Lennox | |
| 6,379,353 B1 | 4/2002 | Nichols | |
| 6,459,937 B1 | 10/2002 | Morgan et al. | |
| 6,478,793 B1 * | 11/2002 | Cosman et al. | 606/34 |
| 6,979,330 B2 * | 12/2005 | Kelly et al. | 606/41 |
| 2003/0109865 A1 | 6/2003 | Greep et al. | |
| 2003/0118649 A1 | 6/2003 | Gao et al. | |
| 2003/0195503 A1 | 10/2003 | Jain et al. | |
| 2004/0096662 A1 | 5/2004 | Lanphere et al. | |
| 2004/0161466 A1 | 8/2004 | Lewis et al. | |
| 2004/0186468 A1 | 9/2004 | Edwards | |

(Continued)

FOREIGN PATENT DOCUMENTS

WO WO2004082749 A2 9/2004

(Continued)

OTHER PUBLICATIONS

PCT International Search Report for PCT/US2008/083665, Applicant: Boston Scientific Scimed, Inc., Form PCT/ISA/210 and 220, dated Mar. 24, 2009 (7 pages).

(Continued)

*Primary Examiner* — Kennedy J Schaetzle
(74) *Attorney, Agent, or Firm* — Vista IP Law Group LLP

(57) ABSTRACT

Tissue ablation probes and methods for treating tissue are provided. The tissue ablation probe comprises an elongated probe shaft, at least one electrode carried by the distal end of the probe shaft, and a pharmaceutical agent carried by the probe shaft. The pharmaceutical agent may be disposed on the electrode(s), the probe shaft, or a releasable portion associated with the electrode or the probe shaft. A method for treating tissue comprises introducing a tissue ablation probe to a tissue site, operating the tissue ablation probe to ablate tissue at the tissue site, and releasing a pharmaceutical agent from the tissue ablation probe at the tissue site.

20 Claims, 15 Drawing Sheets

U.S. PATENT DOCUMENTS

| | | |
|---|---|---|
| 2004/0215130 A1 | 10/2004 | Rioux et al. |
| 2005/0020965 A1 | 1/2005 | Rioux et al. |
| 2005/0090732 A1 | 4/2005 | Ivkov et al. |
| 2005/0196449 A1 | 9/2005 | DiCarlo et al. |
| 2005/0228468 A1 | 10/2005 | Macoviak et al. |
| 2005/0245924 A1* | 11/2005 | Swoyer et al. .......... 606/41 |
| 2006/0009404 A1 | 1/2006 | Williams |

FOREIGN PATENT DOCUMENTS

| | | | |
|---|---|---|---|
| WO | WO 2004082497 | A1 | 9/2004 |
| WO | WO 2007030433 | A2 | 3/2007 |
| WO | WO 2007030433 | A3 | 3/2007 |
| WO | WO 2007144004 | A1 | 12/2007 |

OTHER PUBLICATIONS

PCT Written Opinion of the International Search Authority for PCT/US2008/083665, Applicant: Boston Scientific Scimed, Inc., Form PCT/ISA/237, dated Mar. 24, 2009 (5 pages).

PCT International Preliminary Report on Patentability (Chapter I of the Patent Cooperation Treaty) for PCT/US2008/083665, Applicant: Boston Scientific Scimed, Inc., Form PCT/IB/326 and 373, dated May 27, 2010 (7 pages).

* cited by examiner

ABLATION PROBE FOR DRUG RELEASE IN TISSUE ABLATION PROCEDURES

RELATED APPLICATION

This Application claims priority to U.S. Provisional Patent Application No. 60/988,709 filed on Nov. 16, 2007. The above-noted Patent Application is incorporated by reference as if set forth fully herein.

FIELD OF THE INVENTION

The field of the invention relates to medical devices, and more particularly, to apparatus and methods for delivering therapeutic agents to a site within a body.

BACKGROUND

The delivery of radio frequency (RF) energy to target regions within solid tissue is known for a variety of purposes of particular interest to the present invention. In one particular application, RF energy may be delivered to diseased regions (e.g., tumors) for the purpose of ablating predictable volumes of tissue with minimal patient trauma.

RF ablation of tumors is currently performed using one of two core technologies. The first technology uses a single needle electrode, which when attached to a RF generator, emits RF energy from an exposed, uninsulated portion of the electrode. The second technology utilizes multiple needle electrodes, which have been designed for the treatment and necrosis of tumors in the liver and other solid tissues. U.S. Pat. No. 6,379,353 discloses such a probe, referred to as a LeVeen Needle Electrode™, which comprises a cannula and an electrode deployment member reciprocatably mounted within the delivery cannula to alternately deploy an electrode array from the cannula and retract the electrode array within the cannula. Using either of the two technologies, the energy that is conveyed from the electrode(s) translates into ion agitation, which is converted into heat and induces cellular death via coagulation necrosis. The ablation probes of both technologies are typically designed to be percutaneously introduced into a patient in order to ablate the target tissue.

Following ablation of the target tissue, a transition zone, also described as a hemorrhagic ring, may remain between the dead ablated tissue and live tissue. Over time, the cells in the transition zone may die, or they may continue to live. Should the cells in the transition zone live, there is a risk that the cells carry the same disease as the ablated tissue and thus perpetuate the disease in healthy tissue. Without any preventative treatment, the diseased cells, and any healthy tissue to which the disease spreads, may require one or more follow-up ablation treatments.

To treat any remaining diseased cells, it is known in the art, for example, to follow an ablation procedure with additional treatment in the form of an ingested pharmaceutical agent. These ingested agents, however, circulate the body to locate any remaining diseased tissue, instead of being directly applied to the diseased tissue. This may delay treatment of the diseased tissue, in addition to possibly exposing healthy tissue to the pharmaceutical agent, which may have a toxic effect on the healthy tissue. Additionally, the pharmaceutical agent may be expelled from the body before the cells in the transition zone develop into diseased cells. It is also known in the art to follow an ablation procedure with an additional procedure in which a pharmaceutical agent is directly deposited in the ablated tissue region. However, depositing the pharmaceutical agent into the ablated tissue region would require focusing deposition of the pharmaceutical agent within the hemorrhagic ring, which may be difficult and burdensome to perform without killing healthy tissue. Furthermore, both examples comprise extra procedures in addition to the ablation procedure that may increase patient trauma.

Therefore, there is a need for preventing tissue surrounding an area of ablated tissue from developing into diseased tissue. There is also a need for treating tissue in conjunction with an ablation procedure to minimize the need for further ablation procedures.

SUMMARY OF THE INVENTION

The present inventions are directed to tissue ablation probes and methods for ablating tissue. The tissue ablation probes carry one or more electrodes that can be used to ablate tissue, and one or more pharmaceutical agents that can be released into the tissue. While the present inventions should not be limited in their broadest aspects, the use of a releasable pharmaceutical agent facilitates placement of the pharmaceutical agent at the region where tissue will or has been ablated by the electrode(s).

In accordance with a first aspect of the present inventions, a tissue ablation probe comprises an elongated probe shaft at least one electrode (e.g., a single electrode or an array of electrodes) carried by the distal end of the probe shaft. In an optional embodiment, the tissue ablation probe further comprises a cannula having an elongated cannula shaft and a lumen within the cannula shaft, wherein the probe shaft is slidably disposed within the cannula lumen, such that the at least one electrode is deployable from the cannula lumen.

The tissue ablation probe further comprises a releasable portion detachable from the electrode(s). In one embodiment, the releasable portion is configured to detach from the at least one electrode in response to electrical energy conveyed through the electrode. In this manner, the electrical energy may have the dual function of ablating tissue and detaching the releasable portion. The releasable portion may be attached to the electrode(s) in any one of a variety of manners. For example, the releasable portion is attached to the electrode(s) with a heat-degradable adhesive. As another example, the releasable portion is attached to the electrode(s) via an electrolytically disintegratable link. Other means of attaching releasable portions to electrode(s), such as mechanical activation, shape memory metal or shape memory polymer latches, etc., can be utilized.

The tissue ablation probe further comprises a pharmaceutical agent (e.g., a cancer-fighting drug) carried by the releasable portion. The pharmaceutical agent may be associated with the releasable portion in any one of a variety of manners. For example, the pharmaceutical agent may be disposed on the releasable tip or may even at least partially form the releasable portion.

In accordance with a second aspect of the present inventions, a tissue ablation probe comprises an elongated cannula shaft, a lumen within the cannula shaft, an elongated probe shaft slidably disposed within the cannula lumen, and an electrode array carried by a distal end of the probe shaft, wherein the electrode array is deployable from the cannula lumen. The tissue ablation probe further comprises a pharmaceutical agent (e.g., a cancer-fighting drug) carried by the electrode array. The pharmaceutical agent may be carried by the electrode in any one of a variety of manners. For example, the tissue ablation probe may further comprise a releasable portion detachable from at least one electrode of the electrode array, in which case, the pharmaceutical agent may be carried by the releasable portion. Or, the pharmaceutical agent may simply be disposed on the electrode(s).

In accordance with a third aspect of the present inventions, a tissue ablation probe comprises an elongated probe shaft and an electrode array carried by the distal end of the probe shaft. In an optional embodiment, the tissue ablation probe further comprises a cannula having an elongated cannula shaft and a lumen within the cannula shaft, wherein the probe shaft is slidably disposed within the cannula lumen, such that the electrode array is deployable from the cannula lumen. A releasable portion of the electrode array including substantially an entire electrode tine or tines of the array is configured to detach from a distal end of the probe shaft. In one embodiment, the releasable portion of the electrode array is configured to detach from the probe shaft in response to electrical energy conveyed through the electrode array. The releasable portion of the electrode array may be attached to the probe shaft in any one of a variety of manners. For example, the releasable portion of the electrode array may be coupled to the distal end of the probe shaft via a heat-degradable adhesive. As another example, the releasable portion of the electrode array may be coupled to the distal end of the probe shaft via one or more electrolytically disintegratable links. Other means for attaching releasable portions to the distal end of the probe shaft, such as mechanical activation, shape memory metal or shape memory polymer latches, etc., can be utilized. The tissue ablation probe further comprises a pharmaceutical agent (e.g., a cancer-fighting drug) carried by the releasable portion of the electrode array.

In accordance with a fourth aspect of the present inventions, a tissue ablation probe comprises an elongated probe shaft, at least one electrode carried by a distal end of the probe shaft, a releasable portion detachable from the distal end of the probe shaft, and a pharmaceutical agent (e.g., a cancer-fighting drug) carried by the releasable portion. In an optional embodiment, the at least one electrode comprises an array of electrodes, and the tissue ablation probe further comprises a cannula having an elongated cannula shaft and a lumen within the cannula shaft, wherein the probe shaft is slidably disposed within the cannula lumen, such that the electrode array is deployable from the cannula lumen. In this case, the releasable portion may be a tissue piercing tip directly attached to a distal end of the cannula shaft, and another pharmaceutical agent is carried by the electrode array.

In one embodiment, the releasable portion is configured to detach from the distal end of the probe shaft in response to electrical energy conveyed through the electrode. The releasable portion may be coupled to the distal end of the probe shaft in any one of a variety of manners. For example, the releasable portion is coupled to the distal end of the probe shaft via a heat-degradable adhesive. As another example, the releasable portion is coupled to the distal end of the probe shaft via an electrolytically disintegratable link. Other means of attaching releasable portions to probe shafts, such as mechanical activation, shape memory metal or shape memory polymer latches, etc., can be utilized. The pharmaceutical agent may be associated with the releasable portion in any one of a variety of manners. For example, the pharmaceutical agent may be disposed on the releasable portion or may even at least partially form the releasable portion.

In accordance with a fifth aspect of the present inventions, a method of treating tissue comprises introducing any one of the above-described tissue ablation probes to a tissue site, operating the tissue ablation probe to ablate tissue at the tissue site, and releasing or detaching the pharmaceutical agent, or the releasable portion at the tissue site.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE INVENTION

Figure 1:
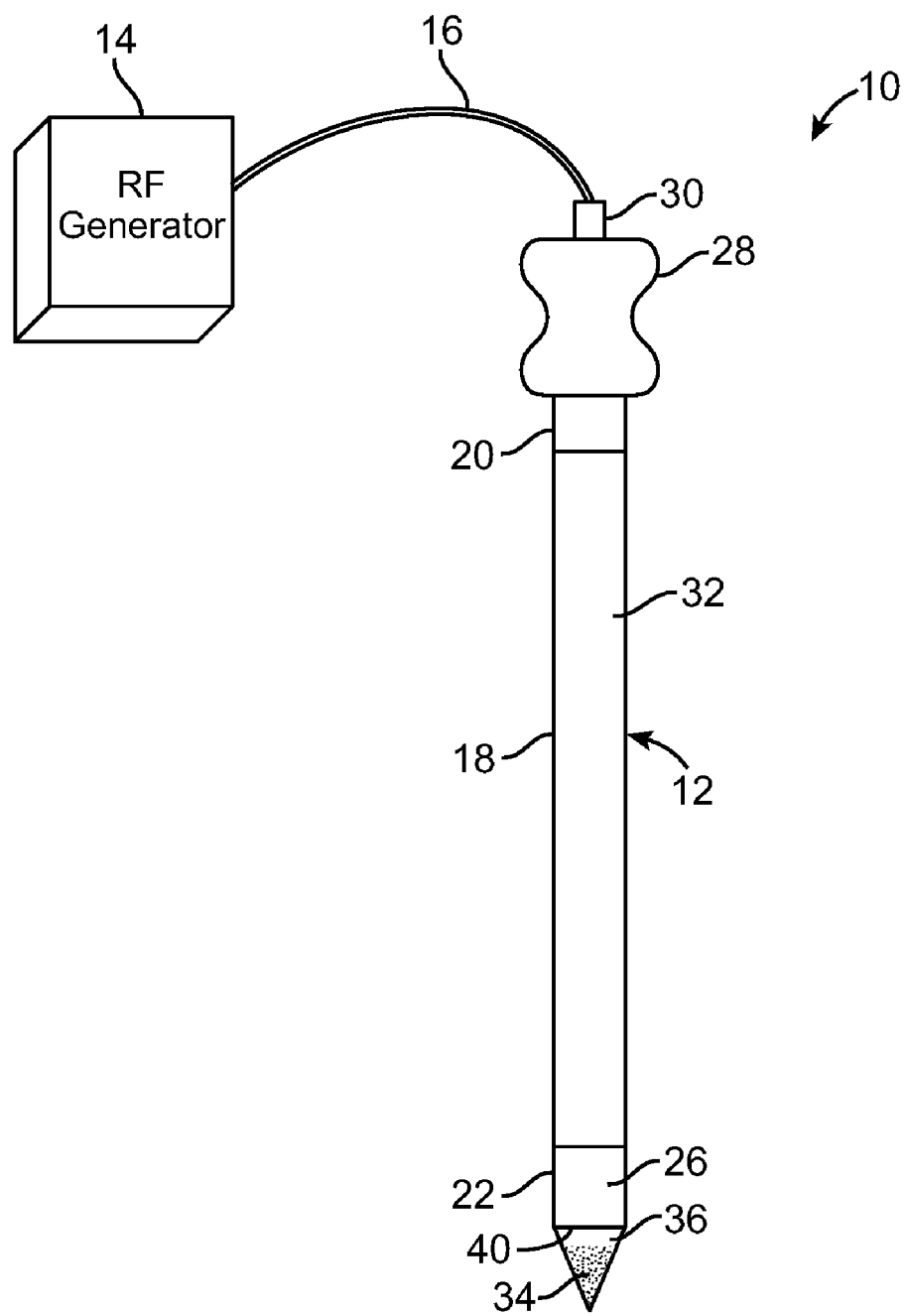
FIG. 1 is a plan view of a tissue ablation system arranged in accordance with one embodiment of the present inventions.

Referring to FIG. 1, a tissue ablation system 10 constructed in accordance with one embodiment of the present inventions, will now be described. The tissue ablation system 10 generally comprises an ablation probe 12 configured for introduction into the body of a patient for ablative treatment of target tissue, a source of ablation energy, and in particular a radio frequency (RF) generator 14, and a cable 16 electrically connecting the ablation probe 12 to the RF generator 14.

The RF generator 14 may be a conventional general purpose electrosurgical power supply operating at a frequency in the range from 300 kHz to 9.5 MHz, with a conventional sinusoidal or non-sinusoidal wave form. Such power supplies are available from many commercial suppliers, such as Valleylab, Aspen, Bovie, and Ellman. Most general purpose electrosurgical power supplies, however, are constant current, variable voltage devices and operate at higher voltages and powers than would normally be necessary or suitable. Thus, such power supplies will usually be operated initially at the lower ends of their voltage and power capabilities, with voltage then being increased as necessary to maintain current flow. More suitable power supplies will be capable of supplying an ablation current at a relatively low fixed voltage, typically below 200 V (peak-to-peak). Such low voltage operation permits use of a power supply that will significantly and passively reduce output in response to impedance changes in the target tissue. The output will usually be from 5 W to 300 W, usually having a sinusoidal wave form, but other wave forms would also be acceptable. Power supplies capable of operating within these ranges are available from commercial vendors, such as Boston Scientific Corporation. Preferred power supplies are models RF-2000 and RF-3000, available from Boston Scientific Corporation.

The ablation probe 12 comprises an elongated, rigid probe shaft 18 having a proximal end 20 and a distal end 22. For the purposes of this specification, a shaft of a probe is rigid if it is generally not suitable to be advanced along a tortuous anatomical conduit of a patient, as contrasted to, e.g., guidewires and intravascular catheters. The probe shaft 18 has a suitable length, typically in the range from 5 cm to 30 cm, preferably from 10 cm to 25 cm, and an outer diameter consistent with its intended use, typically being from 0.7 mm to 5 mm, usually from 1 mm to 4 mm. In the illustrated embodiment, the probe shaft 18 is composed of an electrically conductive material, such as stainless steel. Alternatively, the probe shaft 18 may be composed of an electrically insulative material, such as plastic.

The ablation probe 12 also comprises an electrically insulative layer 32 disposed on the probe shaft to impart an insulative property to the shaft 18. The insulative layer 32 comprises any material suited for its purpose, such as polyether ether ketone (PEEK) or fluorinated ethylene-propylene (FEP). Preferably, the insulative layer 32 is sized to cover most of the probe shaft 18, with the exception of a distal tip of the probe shaft 18. In this manner, an RF ablation electrode 26 is formed by the exposed portion of the distal tip. Thus, all of the RF energy is focused at the electrode 26 where the targeted tissue presumably lies, while the insulative layer 32 prevents RF energy conducted through the shaft 18 from damaging healthy tissue surrounding the shaft 18. In an alternative embodiment, the electrode 26 is a discrete element mounted on the distal end 22 of the probe shaft 18 via suitable means, such as bonding or welding.

The ablation probe 12 further comprises a handle 28 mounted to the proximal end 20 of the probe shaft 18. The handle 28 is preferably composed of a durable and rigid material, such as medical grade plastic, and is ergonomically molded to allow a physician to more easily manipulate the ablation probe 12. The handle 28 comprises an electrical connector 30 with which the cable 16 (shown in FIG. 1) mates. Alternatively, the RF cable 16 may be hardwired within the handle 28. The electrical connector 30 is electrically coupled to the ablation electrode 26 via the probe shaft 18. Alternatively, if the probe shaft 18 is electrically insulative, the electrical connector 30 can be electrically coupled to the ablation electrode 26 via an internal conductor, such as a wire.

In the illustrated embodiment, the RF current is delivered to the electrode 26 in a monopolar fashion, which means that current will pass from the electrode 26, which is configured to concentrate the energy flux in order to have an injurious effect on the surrounding tissue, and a dispersive electrode (not shown), which is located remotely from the electrode 26 and has a sufficiently large area (typically 130 $cm^2$ for an adult), so that the current density is low and non-injurious to surrounding tissue. The dispersive electrode may be attached externally to the patient, e.g., using a contact pad placed on the patient's flank.

In an alternative embodiment, another electrode (not shown) may be carried on the distal end 22 of the probe shaft 18, along with the electrode 26, in a bipolar fashion. Thus, when the RF energy is conveyed to the electrodes, the RF current passes between the electrodes; i.e., between a positive one of the electrodes and a negative one of the electrodes, thereby concentrating the energy flux in order to have an injurious effect on the tissue between the electrodes. In this bipolar arrangement, the electrodes will have to be electrically insulative from each other, in which case, the electrical connector 30 may be coupled to one or both of the electrodes 26 via separate wires, instead of through the probe shaft 18.

The tissue ablation probe 10 further comprises a pharmaceutical agent 34 (best shown in FIG. 2), and in particular a cancer-fighting drug, such as doxorubicin, carried by the distal end 22 of the probe shaft 18. The pharmaceutical agent 34 is carried by the distal end 22 such that it is releasable from the distal end 22 and may be deposited into the ablated tissue region either during or after a tissue ablation procedure. The pharmaceutical agent 34 remains in the ablated tissue region to treat any surviving diseased tissue, particularly in the hemorrhagic ring.

In one embodiment, the pharmaceutical agent 34 comprises a compound that is released over time, i.e. a time-releasable compound. This may be beneficial as there may not be any immediate indication after a tissue ablation process of whether any diseased tissue in the hemorrhagic ring has survived. The presence of surviving diseased tissue may only become evident over time, and possibly after the surviving diseased tissue has already spread to a significant portion of otherwise healthy tissue. The pharmaceutical agent 34 may thus treat any such surviving tissue more effectively if the agent 34 remains in the ablation region for an extended period. When the pharmaceutical agent 34 comprises a time-releasable compound, the agent 34 is less likely to prematurely dissipate or to be immediately absorbed into the surrounding bodily tissue, thus remaining in the ablated tissue region to treat the surviving diseased tissue.

The pharmaceutical agent 34 may be comprised of several materials, many of which may allow the agent to be released over time. In one embodiment, the pharmaceutical agent 34 comprises a bioabsorbable polymer that it is gradually absorbed by surrounding bodily tissue. In another embodiment, the pharmaceutical agent 34 may comprise a plurality of embolic particles, such as those described in U.S. Publication No. 2005/0020965, which is fully incorporated by reference herein. These embodiments serve as examples of how the pharmaceutical agent 34 may be comprised of a cancer-fighting agent or other treatment agent combined with bioabsorbable materials that regulate the rate at which the treatment agent is dissipated in the surrounding tissue region.

Figure 2:
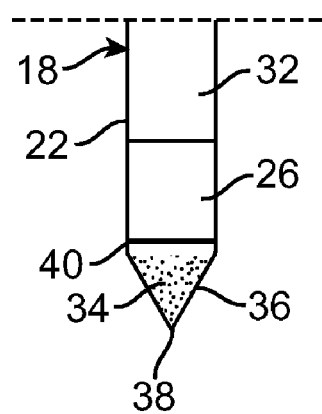
FIG. 2 is a side view of distal end of a tissue ablation probe used in the tissue ablation system of FIG. 1.

In the illustrated embodiment, the pharmaceutical agent 34 is carried on a releasable portion 36 detachable from the distal end 22 of the probe shaft 18, as shown in FIG. 2. For example, the releasable portion 36 may be released from the distal end 22, and in particular into the ablated tissue region, during or after operation of the probe 12. Then, the releasable portion 36 may remain in the ablated tissue region to allow the pharmaceutical agent 34 to dissipate into the surrounding tissue, thus treating the hemorrhagic ring and any other surviving diseased tissue as described above.

In the illustrated embodiment, the releasable portion 36 has a conical shape with a sharpened point 38 to puncture skin, thereby allowing the probe 12 to be percutaneously introduced into a patient. Thus, it may be appreciated that, in this embodiment, the releasable portion 36 has the dual purpose of puncturing tissue to facilitate entry of the probe 12 and carrying the pharmaceutical agent 34 into the ablated tissue region. In alternative embodiments, the releasable portion 36 may have other shapes suitable for its purpose, such as cylindrical, if a tissue penetrating function is not needed.

As best shown in FIG. 2, the releasable portion 36 may be attached to the distal end 22 of the probe shaft 18 with a heat-degradable adhesive 40; that is, the adhesive 40 forms an intermediary between a distal-facing surface of the distal end 22 of the probe shaft 18 and a proximal-facing surface of the releasable portion 36. In one embodiment, the releasable portion 36 and the heat-degradable adhesive 40 are conductive and thus form a portion of the electrode 26. Alternatively, electrical conductivity can be established across electrical connectors left uncovered by the heat-degradable adhesive 40.

Figure 3:
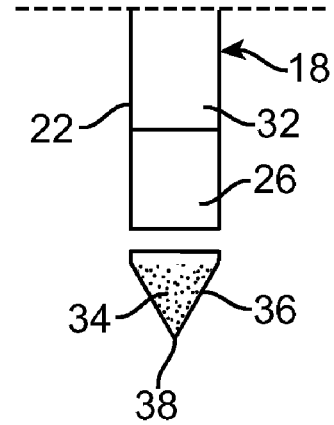
FIG. 3 is a side view of distal end of the tissue ablation probe shown in FIG. 2, particularly showing the detachment of a releasable portion from the probe.

When the adhesive 40 is exposed to heat, the adhesive 40 degrades, allowing the releasable portion 36, and likewise the pharmaceutical agent 34, to detach from the distal end 22 of the probe shaft 18, as illustrated in FIG. 3. In particular, the adhesive 40 may degrade from heat generated by electrical energy conducted on the electrode 26 during a tissue ablation procedure. Thus, electrical energy conducted on the electrode 26 has the dual effect of ablating target tissue and degrading the adhesive 40, so the releasable portion 36 with the pharmaceutical agent 34 may be released into the ablated tissue region.

The releasable portion 36 may comprise a variety of materials suitable for carrying the pharmaceutical agent 34. One such material is a biocompatible metal. When the releasable portion 36 is released from the distal end 22 of the probe shaft 18, the biocompatible metal may remain in bodily tissue without imparting any significant negative effects, even after the pharmaceutical agent 34 has been fully dissipated into the surrounding bodily tissue.

Alternatively, the releasable portion 36 may be comprised of a biodegradable polymer or other biocompatible and/or biodegradable materials. It may be desired that such materials are heat-resistant, so that the releasable portion 36 may remain intact in the presence of heat generated from the electrode 26. In yet another embodiment, the pharmaceutical agent 34 may partially or wholly form the releasable portion 36.

The releasable portion 36 may carry the pharmaceutical agent 34 in several ways. The pharmaceutical agent 34 may be disposed on the releasable portion 36, for example, by coating the releasable portion 36, either wholly, or as shown in FIGS. 1-3, or partially.

Figure 4:
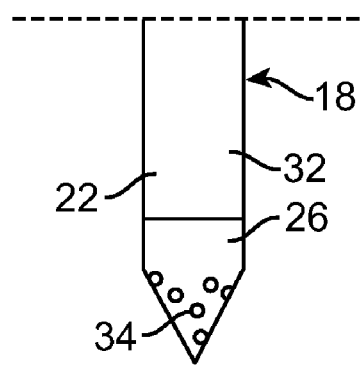
FIG. 4 is a side view of a distal end of another tissue ablation probe that can be used in the tissue ablation system of FIG. 1.

In an alternative embodiment, illustrated in FIG. 4, instead of disposing the pharmaceutical agent 34 over the releasable portion 36, the pharmaceutical agent 34 takes the form of releasable "seeds" distributed over the distal end 22 of the probe shaft 18, and in particular, the electrode 26. For example, the seeds 34 may be attached to the electrode 26 with heat-degradable adhesive (not shown) that allows the seeds 34 to be released from the electrode 26 into the ablated tissue region in the presence of heat. In this embodiment, the distal end 22 may further comprise indentations (not shown) for housing the seeds 34.

Figure 5:
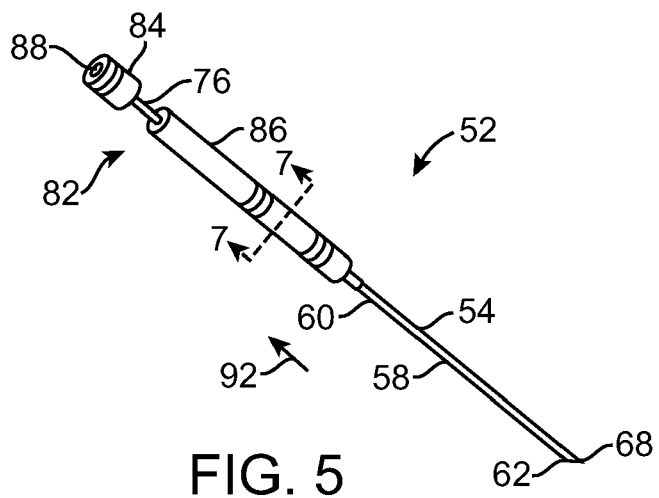
FIG. 5 is a perspective view of another tissue ablation probe that can be used within the tissue ablation system of FIG. 1, wherein an electrode array is particularly shown retracted.
Figure 6:
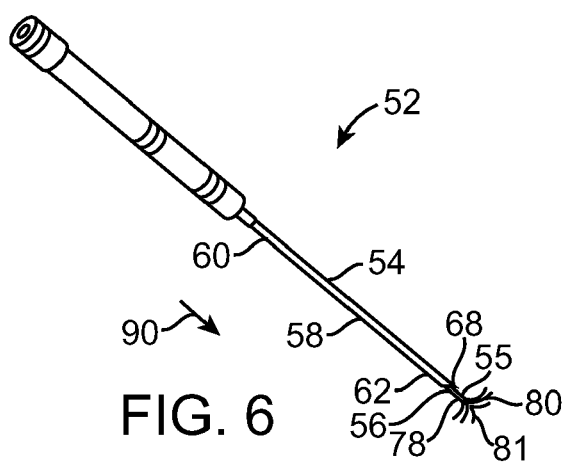
FIG. 6 is a perspective view of the tissue ablation probe of FIG. 5, wherein the electrode array is particularly shown deployed.

Another tissue ablation probe 52 that can be used in conjunction with the RF generator 14 to create an alternative tissue ablation system will now be described. As illustrated in FIGS. 5-6, the tissue ablation probe 52 includes an elongated cannula 54 and an inner probe 55 slidably disposed within the cannula 54.

Figure 7:
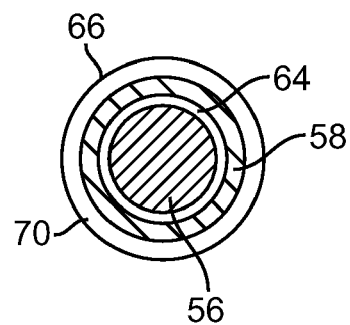
FIG. 7 is a cross-sectional view of the tissue ablation probe of FIG. 5, taken along the line 7-7.

The cannula 54 includes an elongate shaft 58 having a proximal end 60, a distal end 62, and a central lumen 64 (shown in FIG. 7). The cannula shaft 58, itself, is composed of an electrically conductive material, such as stainless steel. The material from which the cannula shaft 58 is composed is preferably a rigid or semi-rigid material, such that the ablation probe 52 can be introduced through solid tissue to a target tissue site. The distal end 62 of the cannula shaft 58 comprises a tissue-penetrating tip 68, which allows the ablation probe 52 to be more easily introduced through tissue, while minimizing tissue trauma. Alternatively, the ablation probe 52 may be introduced through the tissue with the aid of another cannula and trocar assembly, in which case, the cannula shaft 58 may be composed of a flexible material, and the distal end 62 may be blunted. The cannula shaft 58 has a suitable length, typically in the range from 5 cm to 30 cm, preferably from 10 cm to 25 cm, and an outer diameter consistent with its intended use, typically being from 0.7 mm to 5 mm, usually from 1 mm to 4 mm.

The inner probe 55 is slidably disposed within the cannula lumen 64 and includes an elongate shaft 56 having a proximal end 76, a distal end 78, and an electrode array 80 comprising a plurality of tines 81 carried by the distal end 78 of the probe shaft 56. Like the cannula shaft 58, the inner probe shaft 56 is composed of an electrically conductive material, such as stainless steel. The inner probe shaft 56 is composed of a suitably rigid material, so that it has the required axial strength to slide within the cannula lumen 64.

The ablation probe 52 further includes a handle assembly 82, which includes a handle member 84 mounted to the proximal end 76 of the inner probe shaft 56, and a handle sleeve 86 mounted to the proximal end 60 of the cannula 54. The handle member 84 is slidably engaged with the handle sleeve 86 (and the cannula 54). The handle member 84 and handle sleeve 86 can be composed of any suitable rigid material, such as, e.g., metal, plastic, or the like. The handle assembly 82 also includes an electrical connector 88 mounted within the handle member 84. The electrical connector 88 is electrically coupled to the electrode array 80 via the inner probe shaft 56. The electrical connector 88 is configured for mating with the proximal end of the RF cable 16 (shown in FIG. 1). Alternatively, the RF cable 16 may be hardwired within the handle member 84. Like the previously described ablation probe 12, RF current may be delivered to the electrode array 80 in a monopolar fashion.

It may be readily appreciated that longitudinal translation of the probe shaft 56 relative to the cannula 54 in a distal direction 90 can be achieved by holding the handle sleeve 86 and displacing the handle member 84 in the distal direction 90, thereby deploying the electrode array 80 from the distal end 62 of the cannula shaft 58 (FIG. 6), and longitudinal translation of the probe shaft 56 relative to the cannula 54 in a proximal direction 92 can be achieved by holding the handle sleeve 86 and displacing the handle member 84 in the proximal direction 92, thereby retracting the probe shaft 56 and the electrode array 80 into the distal end 62 of the cannula 54 (FIG. 5). Further details regarding electrode array-type probe arrangements are disclosed in U.S. Pat. No. 6,379,353, which has previously been incorporated herein by reference.

The tissue ablation probe 52 further comprises the pharmaceutical agent 34 disposed on a distal portion of the probe 52. The pharmaceutical agent 34 may comprise a time-releasable compound, and may further comprise a bioabsorbable polymer, an embolic particle, or other embodiments, as discussed above.

Figure 8:
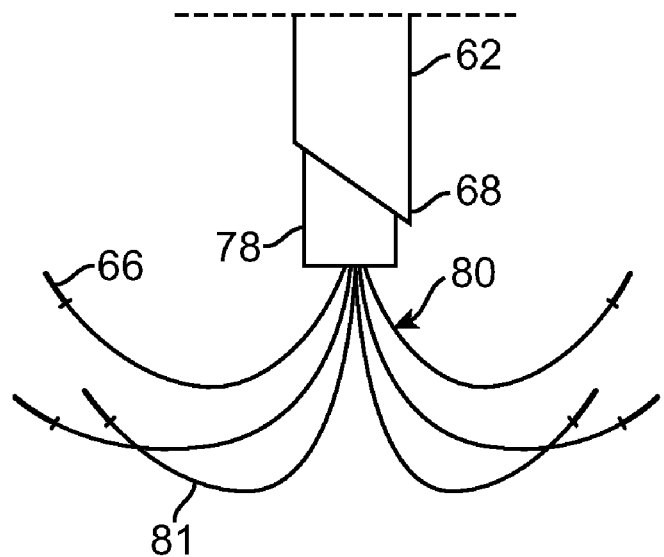
FIG. 8 is a side view of the distal end of one embodiment of the tissue ablation probe in FIG. 5.

As illustrated in FIG. 8, the pharmaceutical agent 34 may be carried on a plurality of releasable portions 66 that are releasably attached to all or a portion of tines 81 in the electrode array 80. In the embodiment shown in FIG. 8, the releasable portions 66 include distal tips of the tines 81. In one embodiment, the releasable portions 66 are conductive and thus form a portion of the electrode array 80. The releasable portions 66 may also have sharpened distal tips (not shown) in order to penetrate surrounding tissue.

Figure 9:
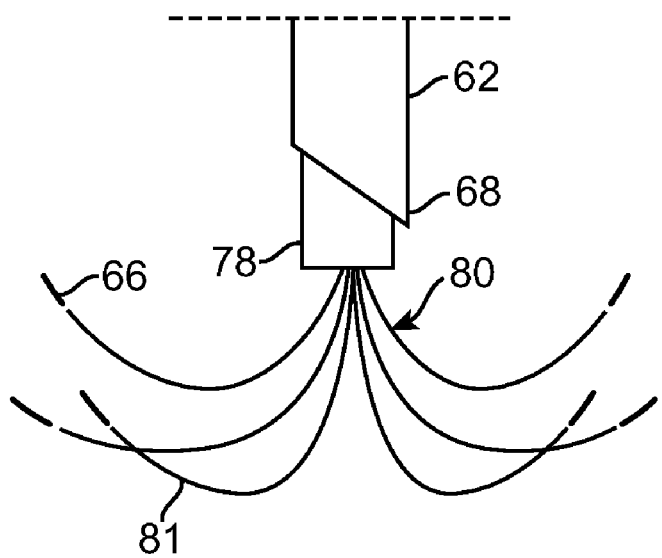
FIG. 9 is a side view of the tissue ablation probe in FIG. 8, wherein releasable portions are detached from the electrode array.

This embodiment has the benefit of having multiple releasable portions 66 that can be released into multiple sites in the ablated tissue region. Additionally, the deployment of the electrode array 80 may cause parts of the releasable portions 66 to become implanted in the target tissue region, causing the releasable portions 66 to be more stationary for treating tissue in that region. Furthermore, the electrode array 80 structure allows the releasable portions 66 to be released from the array 80 in an approximate ring formation, as shown in FIG. 9. Thus, the releasable portions 66 are deposited in a pattern approximating that of the hemorrhagic ring, which may increase the efficiency with which the pharmaceutical agent 34 treats any surviving diseased cells in the hemorrhagic ring.

As illustrated in FIG. 8, each releasable portion 66 may be attached to the tines 81 with a heat-degradable adhesive (not shown), allowing the releasable portions 66 to be detached when heat generated on the electrode array 80 causes the adhesive to degrade, as shown in FIG. 9. If the releasable portions 66 form a portion of the electrode array 80, it may be desirable for the adhesive to be electrically conductive, so that RF energy may be conducted to the releasable portions 66 for ablating a larger region of tissue.

Figure 10:
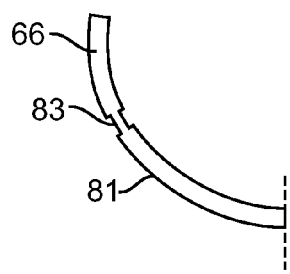
FIG. 10 is a side view of an alternative electrode tine of the tissue ablation probe of FIG. 5.

In another embodiment, illustrated in FIG. 10, each of the releasable portions 66 may be attached to the tines 81 with an electrolytically disintegratable link 83 (enlarged for illustration). The link 83 is severable by electrolysis in an aqueous environment, such as bodily tissue. The link 83 may be composed of steel, stainless steel, nickel, nickel/titanium alloys, or other materials which will electrolytically dissolve as their ions are transferred, i.e., as electrolytic action occurs in an aqueous fluid medium. As electricity is conveyed to the electrode array 80, electrolytic action causes the link 83 to disintegrate and detach the releasable portion 66.

While the above-described embodiments of the releasable portions 66 may include a variety of forms, it is preferable that when the releasable portion 66 is releasably attached to the electrode array 80, the releasable portion 66 has a rod-like shape with a gauge approximate to that of the electrode tines 81. This is so the electrode array 80 may be easily deployed from the distal end 62 of the cannula 54. As described above, the releasable portion 66 may also comprise a variety of materials, such as biocompatible or bioabsorbable metals, polymers, and/or ceramics. Alternatively, the pharmaceutical agent 34 may partially or wholly form the releasable portion 66, as previously described.

Also as previously described, the releasable portions 66 may carry the pharmaceutical agent 34 in several ways when the releasable portions 66 are releasably attached to the electrode array 80. For example, the pharmaceutical agent 34 may be disposed over the releasable portions 66 by coating the releasable portions 66, as described above.

Figure 11:
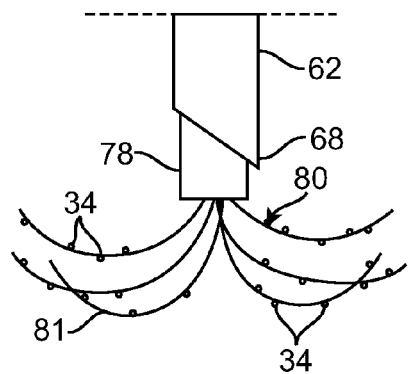
FIG. 11 is a side view of the distal end of another embodiment of the tissue ablation probe in FIG. 5.

As an alternative to having a releasable portion 66, the pharmaceutical agent 34 may be disposed on and released from the electrode array 80. For example, as illustrated in FIG. 11, the pharmaceutical agent 34 may take the form of seeds distributed over the electrode array 80. The seeds 34 may be releasably attached to the electrode array 80 with heat-degradable adhesive (not shown), so that the seeds 34 are released into the ablated tissue region when the adhesive degrades from heat generated on the electrode array 80.

Figure 12A:
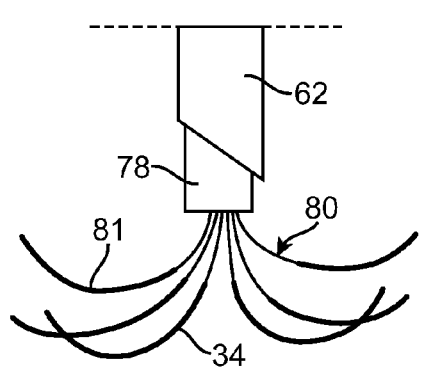
FIGS. 12A and 12B are side views of a distal end of still another embodiment of the tissue ablation probe in FIG. 5, with FIG. 12B particularly showing detachment of the releasable electrode array from the probe.
Figure 12B:
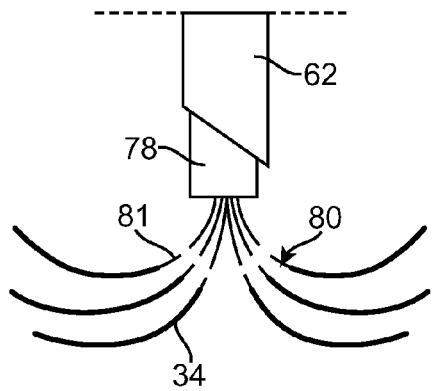

In another embodiment, shown in FIGS. 12A and 12B, the releasable portion 66 includes substantially an entire tine 81 or tines 81 of the electrode array 80. In the illustrated embodiment, portions of the tines 81 remain attached to the distal end 78 of the probe shaft 56, as shown in FIG. 12A. Thus, when the releasable portion 66, in this case tines 81 of the array 80, detaches from the probe shaft 56 as shown in FIG. 12B, the tines 81 may remain in the ablated tissue region even when the probe shaft 56 is removed from the patient while the pharmaceutical agent 34 dissipates. The releasable portion 66 of the electrode array 80 may be releasably attached with a heat-degradable adhesive (not shown), which may be electrically conductive, as previously described. Thus, the releasable portion of the electrode array 80 carrying the pharmaceutical agent 34 detaches in response to electrical energy conducted through the array 80.

In another embodiment, the releasable portion 66 of the array 80 may be releasably attached to a stationary portion of the array 80 with the electrolytically disintegratable link 83, similar to that shown in FIG. 10, such that detachment results when the link 83 disintegrates in response to electricity conducted through the array 80. In still another embodiment, the releasable portion 66 can be mechanically released by coupling the tines 81 to the remaining portion of the electrode array 80 via a mechanical connection (e.g., an anchor and hook) that activates when the electrode array 80 is fully deployed. In this case, ablation can occur when the electrode array 80 is less than fully deployed, after which, the electrode array 80 can be fully deployed to detach the releasable portion 66 from the probe shaft 78.

The releasable portion 66 of the electrode array 80 may be comprised of, for example, a biocompatible or bioabsorbable metal, polymer, and/or ceramic. Thus, when the releasable portion 66 of the array 80 detaches from the distal end 78 of the probe shaft 56 to remain in the ablated tissue region, the array 80 will not impart any significant negative effects on surrounding bodily tissue.

Figure 13:
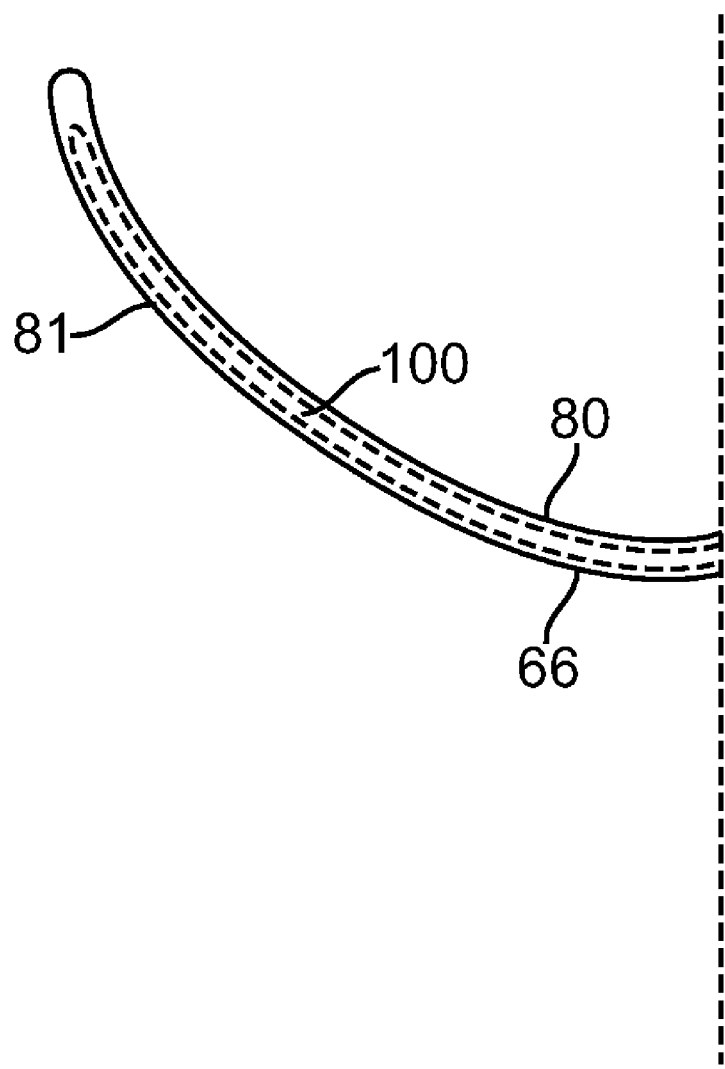
FIG. 13 is a side view of a distal end of still another embodiment of the tissue ablation probe in FIG. 5.

In an alternative embodiment, illustrated in FIG. 13 the releasable portion 66 may include a hollow portion 100 that carries the pharmaceutical agent 34. The hollow portion 100 may be pre-filled with the pharmaceutical agent 34. Alternatively, the hollow portion 100 may be in fluid communication with an additional lumen (not shown) in the probe shaft 56 that carries the pharmaceutical agent 34, such that during or after the delivery of energy to the electrode array 80, the pharmaceutical agent 34 may be injected from the additional lumen into the hollow portion 100. This may be desirable if the pharmaceutical agent 34 is heat-sensitive to prevent degradation during the ablation process.

Thus, the releasable portion 66 of the electrode array 80 carries the pharmaceutical agent 34 upon disengagement and releases the pharmaceutical agent 34 from the hollow portion 100. This may happen immediately, for example, if the pharmaceutical agent 34 exits through an opening in the releasable portion 66, or over time, if the releasable portion 66 is porous, bioabsorbable, or biodegradable. In this embodiment, the releasable portion 66 of the electrode array 80 is connected to the probe 12, for example with the heat-degradable adhesive 40, such that there is a continuous channel in fluid communication with the additional lumen, allowing the hollow portion 100 to receive the pharmaceutical agent 34.

In another embodiment, it may also be desirable for the distal end 22 of the probe 12 to include an opening (not shown) in fluid communication with the additional lumen, such that the pharmaceutical agent 34 may be delivered from the additional lumen through the opening to the target tissue site. This may be desirable if the pharmaceutical agent 34 is heat-sensitive, to ensure there is sufficient pharmaceutical agent 34 that has not been altered by heat from the RF energy to treat the ablated tissue region.

Figure 14:
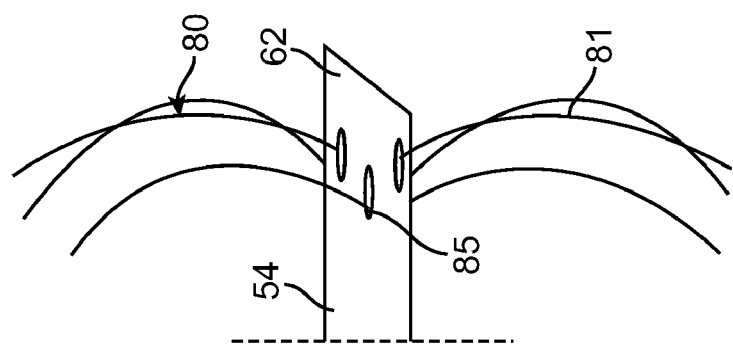
FIG. 14 is a side view of a distal end of another embodiment of the tissue ablation probe in FIG. 5.

In an alternative embodiment, instead of the array 80 being deployed through the distal end 62 of the cannula 54, the array 80 may be deployed through slots 85 on sides of the distal end 62 of the cannula shaft 58, as shown in FIG. 14. In this embodiment, a pharmaceutical agent (not shown) may be carried by releasable portions on the array, or on the array 80, as described above.

Figure 15:
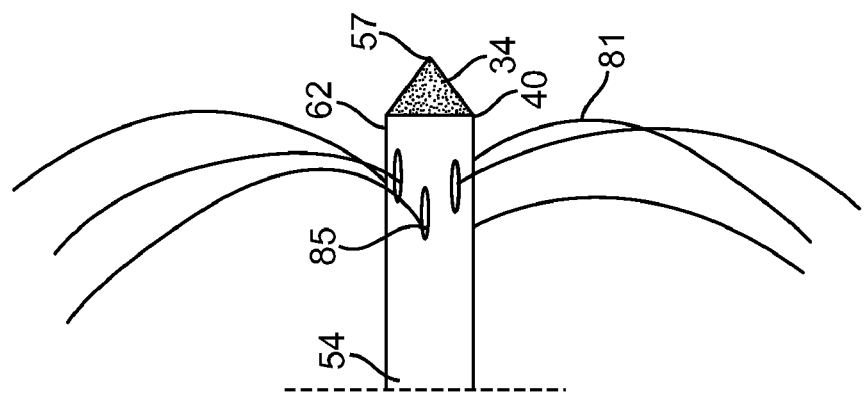
FIG. 15 is a side view of a distal end of still another embodiment of the tissue ablation probe in FIG. 5.

In another embodiment, as shown in FIG. 15, the distal end 62 of the cannula 54 may comprise a closed tissue-penetrating tip 57. This allows the cannula 54 to be more easily introduced through tissue, while preventing tissue coring and minimizing tissue trauma. The tissue-penetrating tip 57 may carry the pharmaceutical agent 34 and thus be releasably attached to the distal end 62 of the cannula 54 with the heat-degradable adhesive 40.

In addition, the cannula 54 further comprises side slots 85, similar to those shown in FIG. 14, such that the when the inner probe shaft 56 is advanced through the cannula 54, the electrode array 80 is deployed through the side slots 85. The electrode array 80 may also have releasable portions 66 carrying the pharmaceutical agent 34, or the array 80 may carry the pharmaceutical agent 34, as described above.

Figure 16:
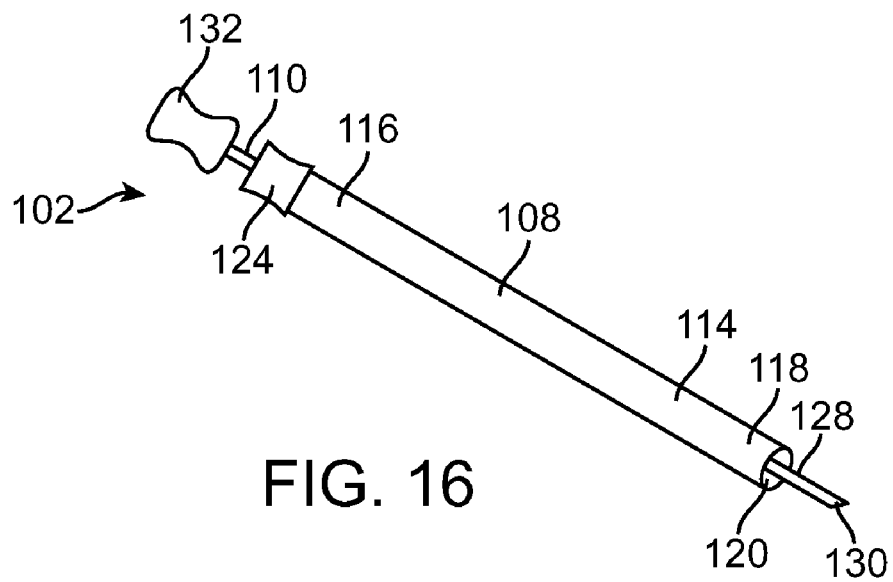
FIG. 16 is a perspective view of part of a co-access probe assembly that can be used within the tissue ablation system of FIG. 1.
Figure 17:
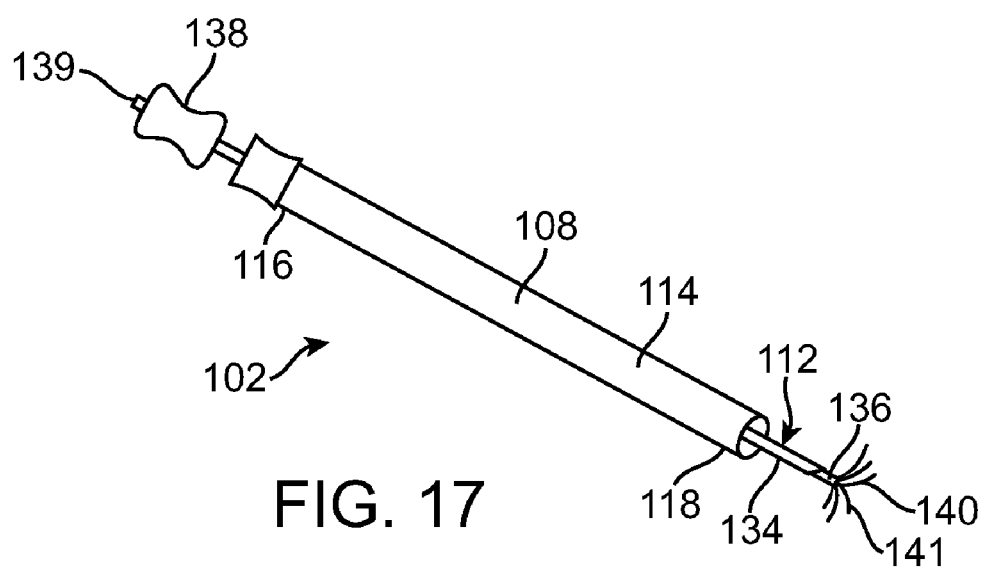
FIG. 17 is a perspective view of another part of the co-access system for use with a tissue ablation probe that can be used within the tissue ablation system of FIG. 1.

As an alternative to the probes 12, 52 described above, a co-access probe assembly 102 may also be used, as shown in FIGS. 16 and 17. The co-access probe assembly 102 comprises a delivery cannula 108, a biopsy stylet 110, and a tissue ablation probe 112. The biopsy stylet 110 and ablation probe 112 are configured to be alternately introduced through the delivery cannula 108 in contact with the tissue to be treated. Additionally, either the biopsy stylet 110, the ablation probe 112, or a separate trocar (not shown) can be used to facilitate the percutaneous introduction of the delivery cannula 108, which has a blunt end.

The delivery cannula 108 comprises a cannula shaft 114 having a proximal end 116 and a distal end 118, and a delivery lumen 120 extending therebetween. The cannula shaft 114 has a suitable length, and may be rigid, semi-rigid, or flexible, depending upon the designed means for introducing the delivery cannula 108 to the target tissue. The delivery cannula 108 further comprises a handle 124 mounted to the proximal end 116 of the cannula shaft 114.

The biopsy stylet 110 comprises a solid elongated shaft 128 with a tissue-penetrating distal tip 130 and a proximal handle piece 132. The biopsy stylet 110 may be operated in a standard manner to obtain a tissue sample. For example, the biopsy stylet 110 may comprise a grooved notch (not shown) configured to extract and hold a tissue sample from a patient. Further details regarding the structure and use of biopsy stylets in association with cannulae are disclosed in U.S. Pat. No. 5,989,196, which is expressly incorporated herein by reference. In an alternative embodiment, if no tissue sample is required, a trocar (not shown) may be used in place of the stylet 110 to penetrate tissue and carry the delivery cannula 108 to the treatment site.

The tissue ablation probe 112 is similar to the tissue ablation probe 52 illustrated in FIGS. 5-7, in that it comprises a cannula 134 and an inner probe shaft 136 slidable within the cannula 134. A proximal handle assembly 138 with an electrical connector 139 can be manipulated to distally advance the inner probe shaft 136 through the cannula 134, thereby deploying an electrode array 140 from the cannula 134, as shown in FIG. 17. In an alternative embodiment, the use of the cannula 134 is foregone, so that the inner probe shaft 136 is slidably disposed in direct contact with the cannula shaft 114.

Similar to the embodiments described above, the pharmaceutical agent 34 may be carried on releasable portions 66 that are releasably attached to tines 141 of the electrode array 140 with a heat-degradable adhesive, or the pharmaceutical agent 34 may comprise seeds 34 releasably attached to the array 140. In another embodiment, the pharmaceutical agent 34 may be disposed on the array 140, wherein at least a portion of the array 140 is releasable from the probe shaft 136, as described above.

Having described the structure of the tissue ablation system 10, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 $cm^3$ to 150 $cm^3$, and often from 2 $cm^3$ to 35 $cm^3$ The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 18A:
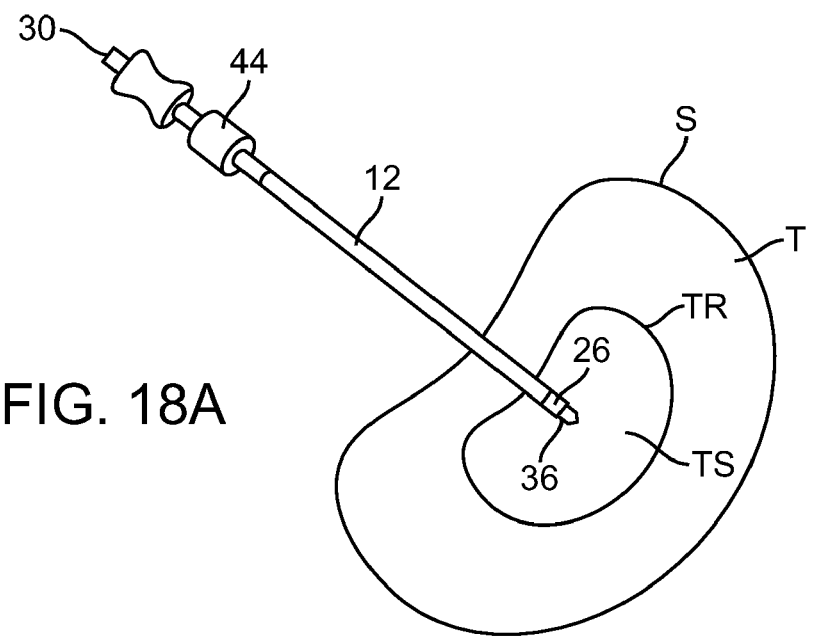
FIGS. 18A-18D illustrate cross-sectional views of one method of using the tissue ablation system of FIG. 1 to treat tissue, wherein the tissue ablation probe of FIG. 2 is particularly used.
Figure 18B:
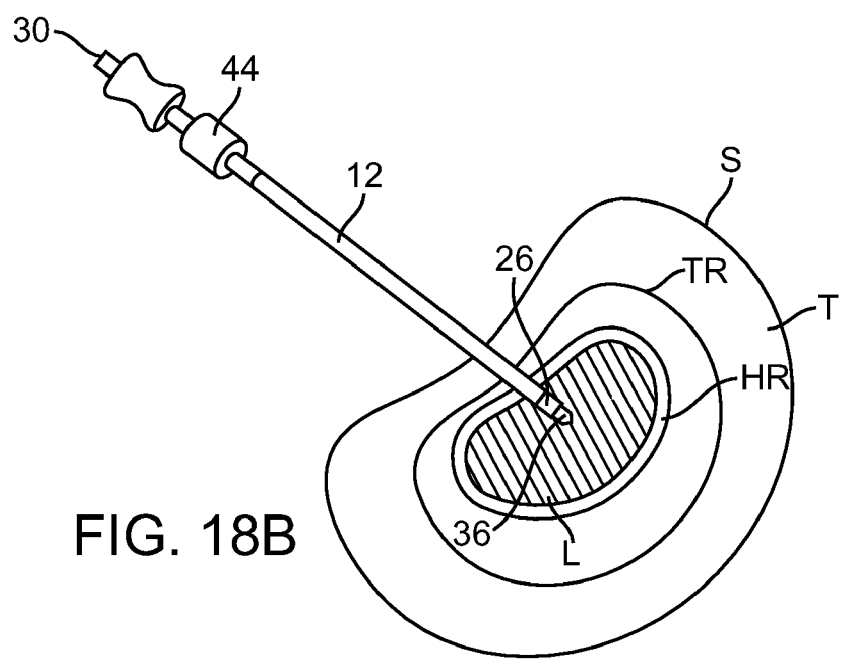

Referring now to FIGS. 18A and 18B, the operation of the tissue ablation system 10 is described in treating a treatment region TR with tissue T located beneath the skin or an organ surface S of a patient. The ablation probe 12 is first introduced through the tissue T under the guidance of a conventional ultrasound imaging device, so that the electrode 26 is located at a target site TS within the treatment region TR, as shown in FIG. 18A. This can be accomplished using any one of a variety of techniques. In the preferred method, a delivery device, such as a probe guide (not shown), is used to guide the ablation probe 12 towards the target site TS. In particular, the probe guide is affixed and aligned relative to the target site TS, and the ablation probe 12 is introduced through the probe guide. Facilitated by the sharpened tip 38 on the releasable tip 36, the ablation probe 12 is percutaneously introduced through the patient's skin until the electrode 26 is located in the treatment region TR.

Once the ablation probe 12 is properly positioned, the cable 16 of the RF generator 14 (shown in FIG. 1) is then connected to the electrical connector 30 of the ablation probe 12, and then operated to transmit RF energy to the electrode 26, thereby ablating the treatment region TR, as illustrated in FIG. 18B. As a result, a lesion L will be created, which will eventually expand to include the entire treatment region TR. The ablation also results in the creation of a hemorrhagic ring HR around the lesion L.

Figure 18C:
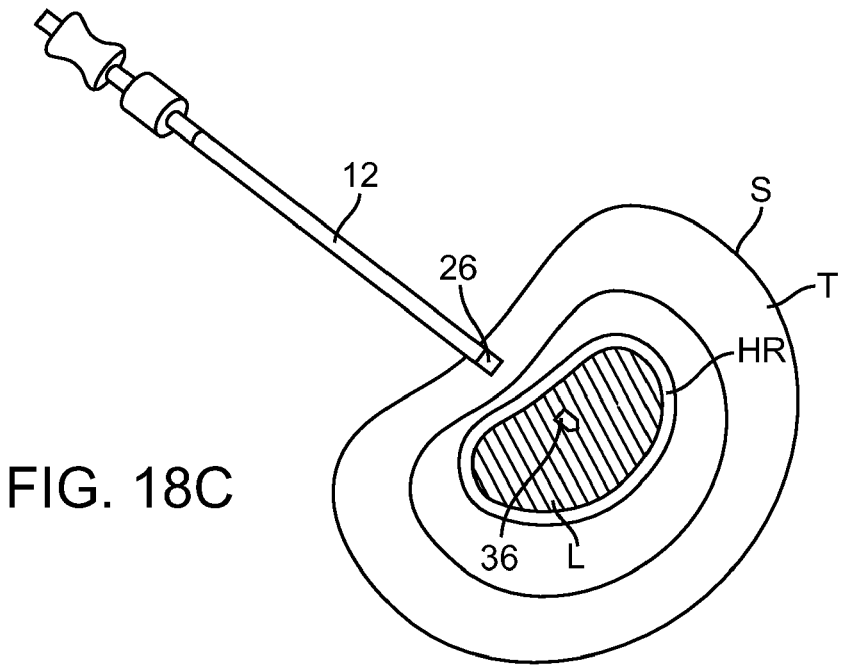
Figure 18D:
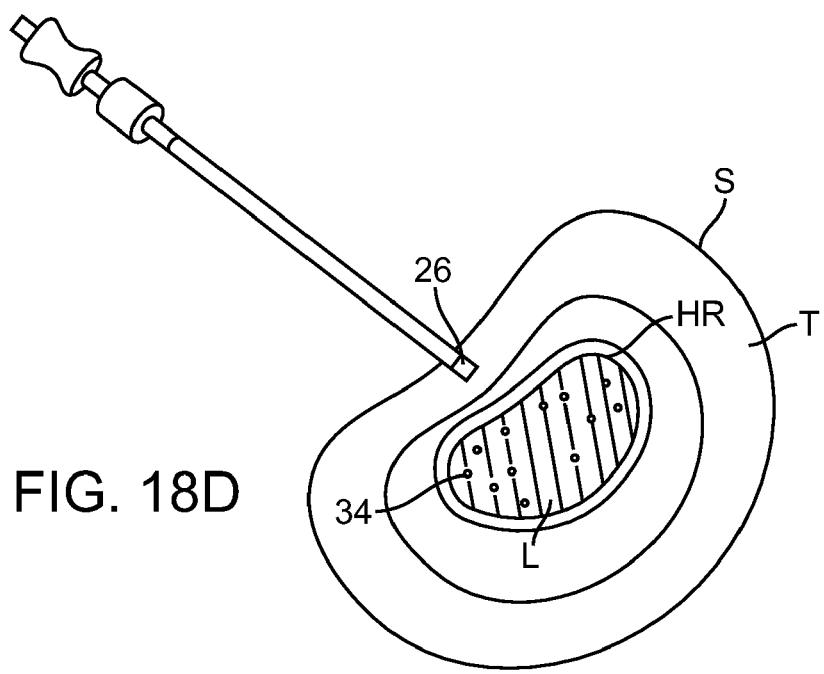

Next, the pharmaceutical agent 34 is released from the ablation probe 12 into the lesion L and hemorrhagic ring HR area. In the illustrated method, as RF energy is transmitted to the electrode 26, the heat generated on the electrode 26 causes the adhesive 40 (shown in FIGS. 2 and 3) to degrade, allowing the releasable portion 36 to be released into the lesion L and hemorrhagic ring HR area, as shown in FIG. 18C. In the embodiment for which the pharmaceutical agent 34 comprises seeds distributed over the releasable portion 36 (shown in FIG. 4), the heat generated on the electrode 26 causes the adhesive that secures the seeds 34 to the releasable portion 36 to degrade, allowing the seeds 34 to be released into the lesion L and hemorrhagic ring HR area, as shown in FIG. 18D.

The pharmaceutical agent 34 may then remain in the lesion L and hemorrhagic ring HR area to be released over time to treat any surviving diseased tissue. The releasable portion 36, if in the embodiment used, may also remain in the ablated tissue region, or it may dissolve or degrade, depending upon the material selected for the releasable portion 36.

Figure 19A:
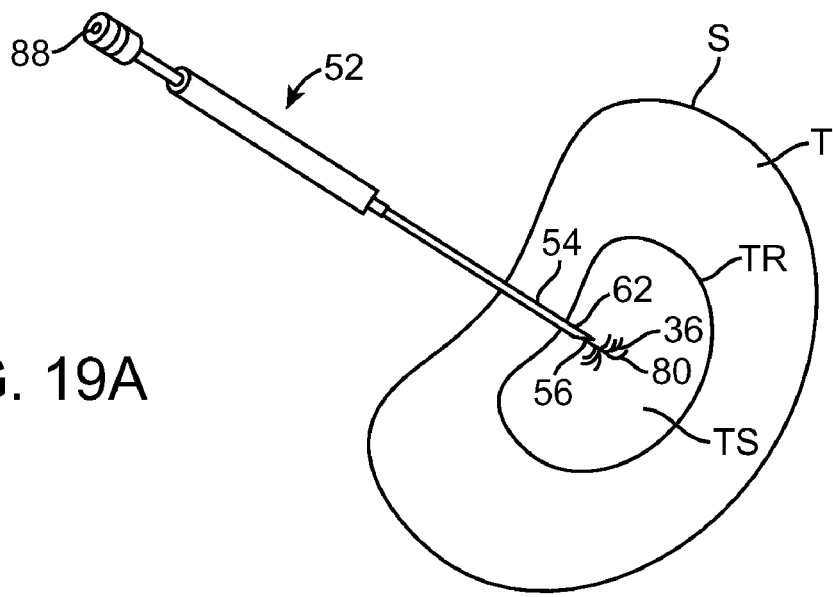
FIGS. 19A-19E illustrate cross-sectional views of another method of using the tissue ablation system of FIG. 1 to treat tissue, wherein the tissue ablation probe of FIG. 5 is particularly used.

In an alternative method, the ablation probe 52 illustrated in FIGS. 5 and 6 may be used to ablate tissue by guiding the distal end 62 of the cannula 54 to the target site TS, after which the inner probe shaft 56 can be distally advanced through the cannula 54 to deploy the electrode array 80 out from the distal end 62 of the cannula 54, as shown in FIG. 19A. Alternatively, using the embodiment shown in FIG. 14, the array 80 may be deployed through the side slots 85 on the distal end 62 of the cannula 54.

Figure 19B:
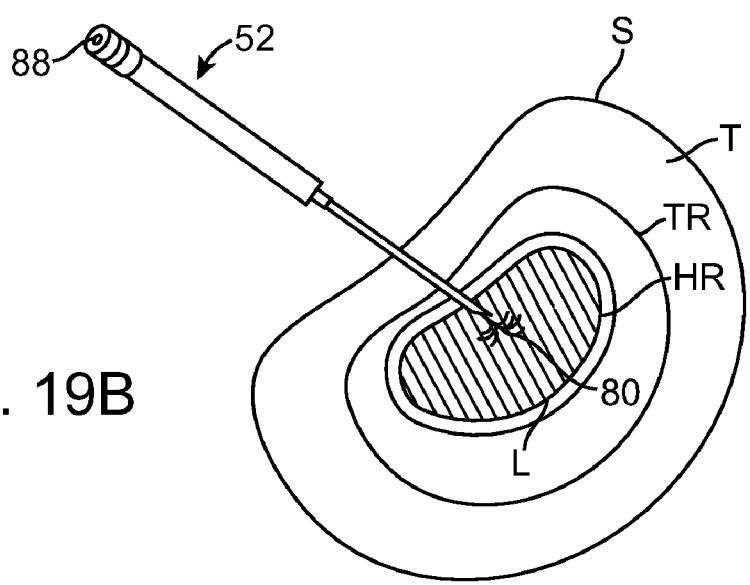

As previously discussed, once the ablation probe 52 is properly positioned, the cable 16 of the RF generator 14 (shown in FIG. 1) is then connected to the electrical connector 88 of the ablation probe 52, and then operated to transmit RF energy to the electrode array 80, thereby ablating the treatment region TR, as illustrated in FIG. 19B. As a result, lesion L will be created, encircled by hemorrhagic ring HR.

Figure 19C:
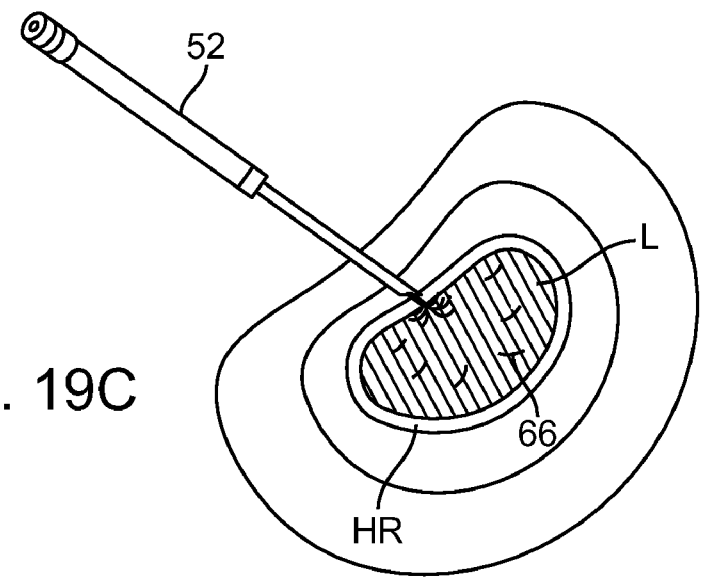

For the embodiment in which the releasable portions 66 are carried on the electrode array 80 (shown in FIGS. 8 and 9), the heat generated on the array 80 by the RF energy causes the adhesive to degrade, allowing the releasable portions 66 to be released into the ablated tissue region, as shown in FIG. 19C. Alternatively, if the releasable portions 66 are attached to the tines 81 of the electrode array 80 via electrolytic links 83 (as shown in FIG. 10), the releasable portions 66 will detach from the tines 81 when the links 83 electrolytically dissolve in response to current flowing through the electrode array 80.

Figure 19D:
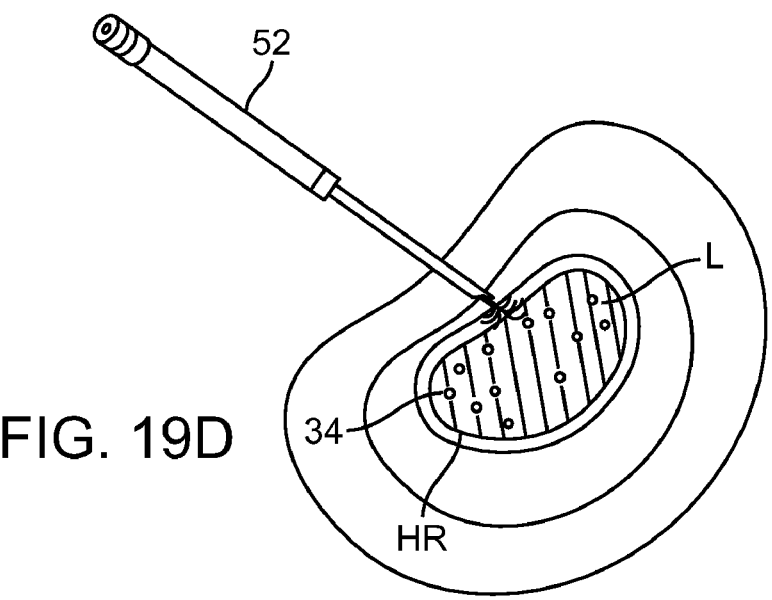

In the embodiment in which the pharmaceutical agent 34 comprises seeds disposed on the array 80 (shown in FIGS. 10 and 11), the heat generated on the array 80 causes the adhesive that secures the seeds 34 to the releasable portions 66 to degrade, allowing the seeds 34 to be released into the ablated tissue region, as shown in FIG. 19D, where the seeds 34 remain to treat any remaining diseased tissue.

Figure 19E:
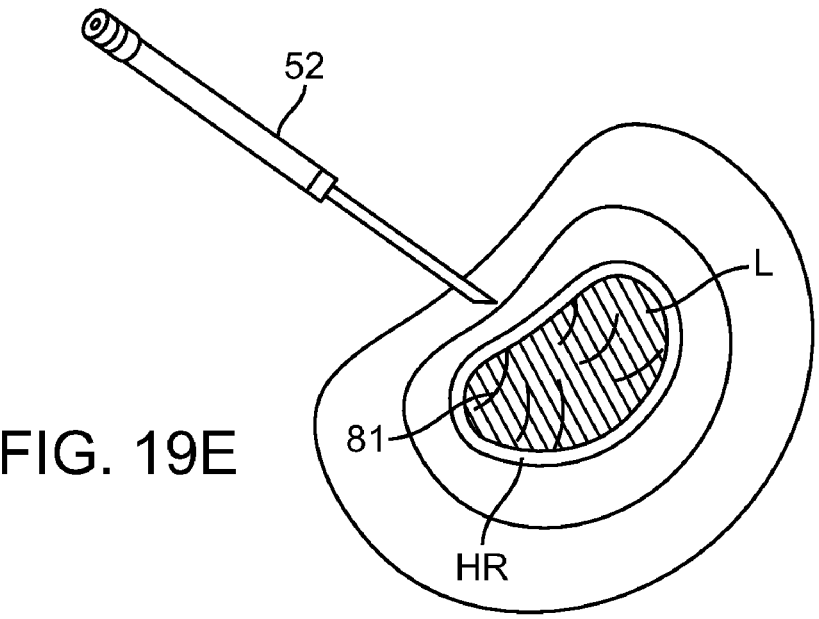

In the embodiment in which the releasable portion 66 includes substantially an entire tine 81 or tines 81 of the electrode array 80, and the pharmaceutical agent 34 coats the releasable portion 66 (shown in FIGS. 12 and 13), the heat generated on the array 80 causes the adhesive to degrade, allowing the tine(s) 81 to be released into the ablated tissue region, as shown in FIG. 19E. The tine(s) 81 may remain in the ablated tissue region, while the pharmaceutical agent 34 dissipates into the ablated tissue region to treat any remaining diseased tissue.

In the embodiment in which the releasable portion 66 includes the hollow portion 100 in communication with an additional lumen, the pharmaceutical agent 34 may be injected from the additional lumen into the hollow portion 100 during or after the RF energy is delivered to the electrode array 80. Alternatively, the pharmaceutical agent 34 may already be carried within the hollow portion 100 of the releasable portion 66. When the releasable portion 66 is released into the ablated tissue region, the pharmaceutical agent 34 is released from the hollow portion 100. In an alternative embodiment, the pharmaceutical agent 34 may be delivered from the additional lumen to the ablated tissue region through the opening at the distal end 22 of the probe 12, to help ensure a sufficient amount of pharmaceutical agent 34 is distributed to the ablated tissue region.

Figure 20:
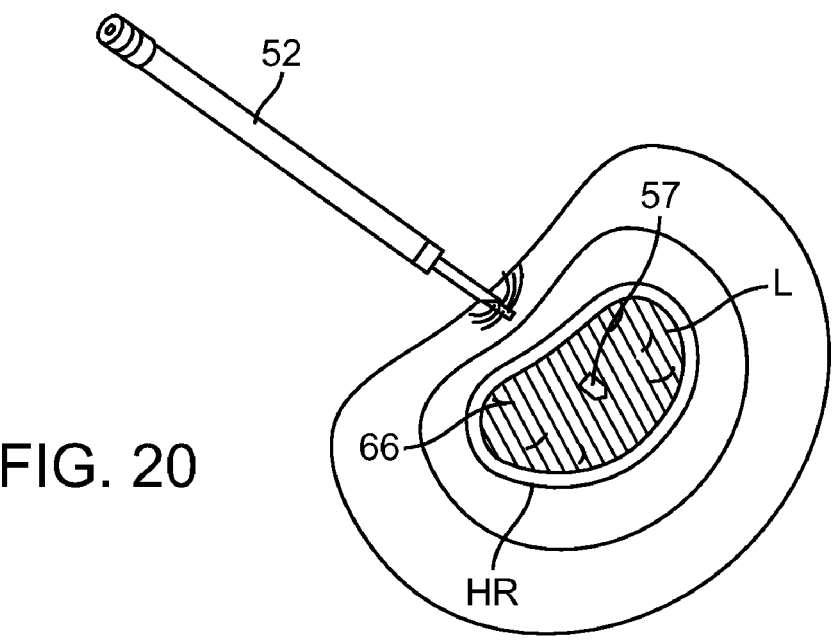
FIG. 20 illustrates a cross-sectional view of another method of using the tissue ablation system of FIG. 1 to treat tissue, wherein the embodiment shown in FIG. 15 is particularly used.

Referring to FIG. 20, RF energy is transmitted to the electrode array 80 of the embodiment illustrated in FIG. 15 to ablate the tissue region, creating lesion L encircled by hemorrhagic ring HR. Depending on the embodiment used, the heat generated on the array 80 causes the adhesive 40 (shown in FIG. 15) to degrade, allowing the tip 57 of the cannula 54 to be released into the ablated tissue region.

Figure 21A:
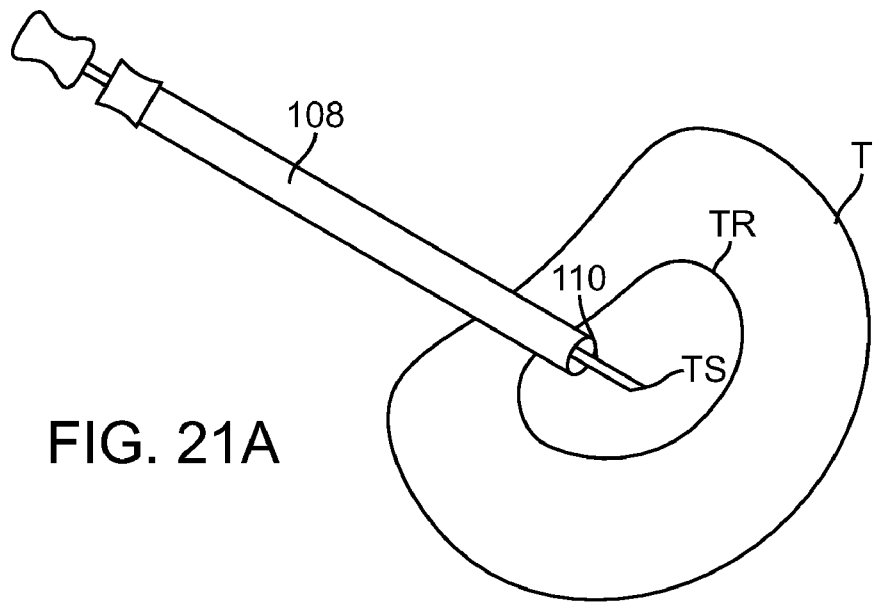
FIGS. 21A-21D illustrate cross-sectional views of another method of using the tissue ablation system of FIG. 1 to treat tissue, wherein the tissue ablation probe of FIG. 16 is particularly used.

In another method, the co-access assembly 102 shown in FIGS. 16 and 17 may be used to ablate tissue. In the preferred method, the biopsy stylet 110 is introduced into the delivery cannula 108, and then the cannula 108 with the stylet 110 is percutaneously introduced through the patient's skin to the treatment region TR, as shown in FIG. 21A. The biopsy stylet 110 is manipulated to retrieve a tissue sample from the patient, and then removed from the delivery cannula 108, while the delivery cannula 108 remains in position. Next, the probe 112 is introduced into the delivery cannula 108 until a distal end of the inner probe shaft 136 is located at the target site TS, after which the inner probe shaft 116 can be distally advanced through the cannula 114 to deploy the electrode array 140, as shown in FIG. 21B.

Alternatively, if a distal end of the inner probe shaft 136 is sharpened, the probe 112 may be introduced into the delivery cannula 108 and then percutaneously introduced through the patient's skin, instead of the stylet 110, and advanced to the treatment region TR. Then, the electrode array 140 may be deployed as described above.

Figure 21B:
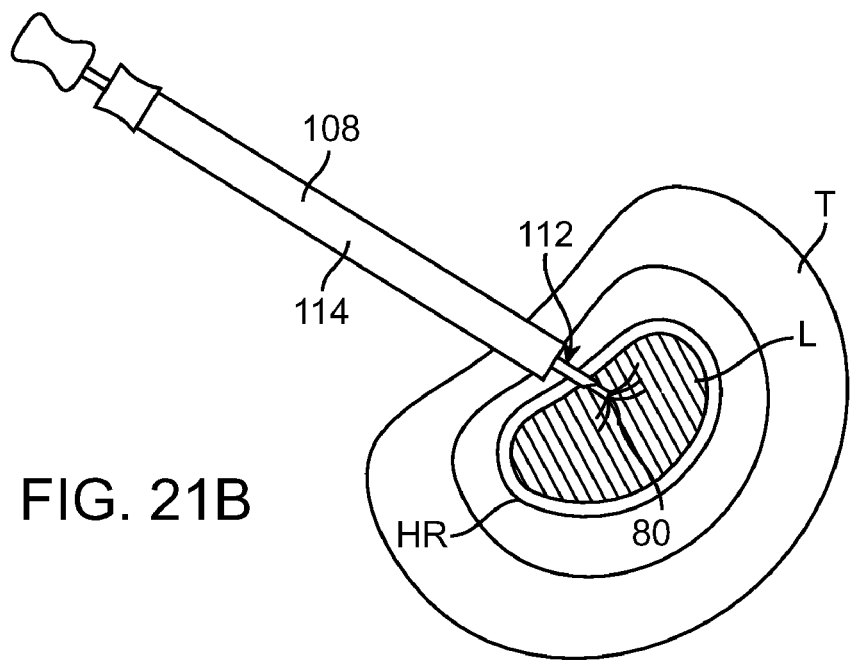

As previously discussed, once the ablation probe 112 is properly positioned, the cable 16 of the RF generator 14 (shown in FIG. 1) is then connected to an electrical connector (not shown) on the ablation probe 112, and then operated to transmit RF energy to the electrode array 140, thereby ablating the treatment region TR, as illustrated in FIG. 21B. As a result, lesion L will be created, encircled by hemorrhagic ring HR.

Figure 21C:
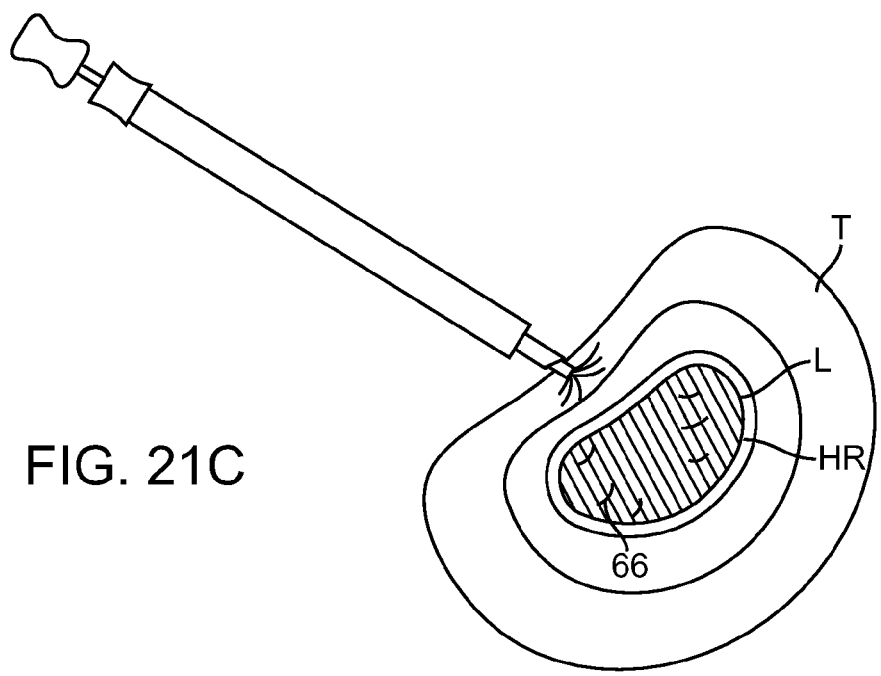

For the embodiment in which the releasable portions 66 are carried on the electrode array 140, the heat generated on the array 140 by the RF energy causes the adhesive 40 to degrade, allowing the releasable portions 66, and thus the pharmaceutical agent 34, to be released into the ablated tissue region, as shown in FIG. 21C. There, the releasable portions 66 and the pharmaceutical agent 34 may remain to treat any surviving diseased tissue.

Figure 21D:
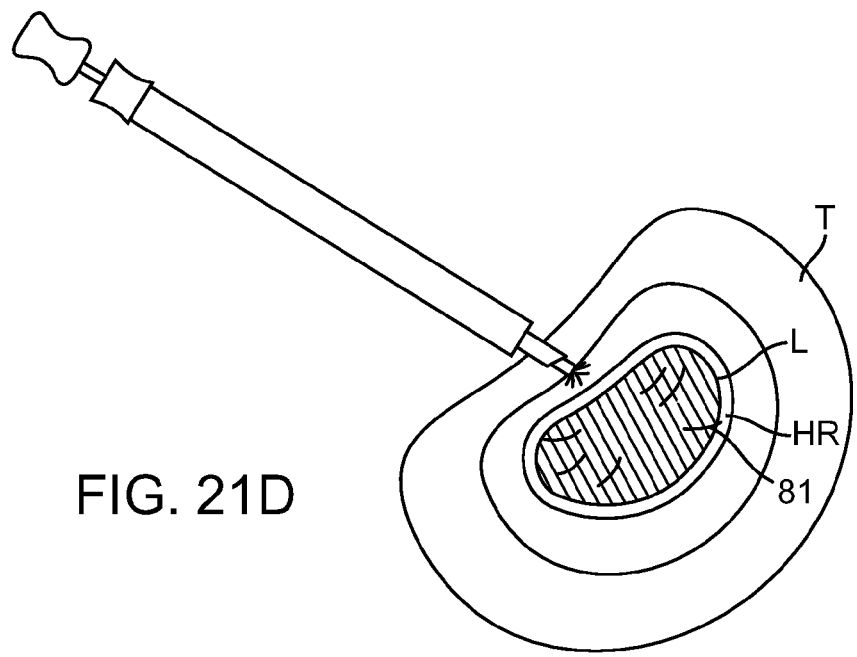

In the embodiment in which the electrode array 140 is releasable from the inner probe shaft 136 and the pharmaceutical agent 34 coats the array 140, the heat generated on the array 140 causes the adhesive 40 to degrade, allowing the tines 141 to be released into the ablated tissue region, as shown in FIG. 21D. The tines 141 may remain in the ablated tissue region, while the pharmaceutical agent 34 dissipates into the ablated tissue region to treat any remaining diseased tissue.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed:

1. A tissue ablation probe, comprising:
   an elongated probe shaft;
   at least one electrode carried by a distal end of the probe shaft;
   a releasable portion detachable from the at least one electrode; and
   a pharmaceutical agent comprising a cancer-fighting drug carried by the releasable portion.

2. The tissue ablation probe of claim 1, wherein the releasable portion forms a part of the at least one electrode.

3. The tissue ablation probe of claim 1, wherein the releasable portion is configured to detach from the at least one electrode in response to electrical energy conveyed through the at least one electrode.

4. The tissue ablation probe of claim 1, wherein the releasable portion is attached to the at least one electrode with an adhesive.

5. The tissue probe of claim 1, wherein the pharmaceutical agent at least partially forms the releasable portion.

6. The tissue ablation probe of claim 1, wherein the pharmaceutical agent is disposed on the releasable portion.

7. The tissue ablation probe of claim 1, wherein the pharmaceutical agent is released over a period of time.

8. The tissue ablation probe of claim 1, wherein the releasable portion is configured to release from the at least one electrode after the at least one electrode has ablated surrounding tissue.

9. The tissue ablation probe of claim 1, wherein the releasable portion is conical in shape.

10. A tissue ablation probe, comprising:
    an elongated probe shaft;
    at least one electrode carried by a distal end of the probe shaft;
    a releasable portion detachable from the distal end of the probe shaft; and
    a pharmaceutical agent comprising a cancer-fighting drug carried by the releasable portion.

11. The tissue ablation probe of claim 10, wherein the releasable portion is a tissue piercing tip directly attached to a distal end of the probe shaft.

12. The tissue ablation probe of claim 10, wherein the at least one electrode comprises a single electrode.

13. The tissue ablation probe of claim 10, wherein the releasable portion forms a portion of the at least one electrode.

14. The tissue ablation probe of claim 10, wherein the releasable portion is configured to detach from the distal end of the probe shaft in response to electrical energy conveyed through the releasable portion.

15. The tissue ablation probe of claim 10, wherein the releasable portion is coupled to the distal end of the probe shaft via an adhesive.

16. The tissue ablation probe of claim 10, wherein the pharmaceutical agent at least partially forms the releasable portion.

17. The tissue ablation probe of claim 10, wherein the pharmaceutical agent is disposed on the releasable portion.

18. The tissue ablation probe of claim 10, wherein the pharmaceutical agent is released over a period of time.

19. The tissue ablation probe of claim 10, wherein the releasable portion is configured to release from the at least one electrode after the at least one electrode has ablated surrounding tissue.

20. The tissue ablation probe of claim 10, wherein the releasable portion is conical in shape.

* * * * *